United States Patent
Matsumoto et al.

(10) Patent No.: US 7,087,273 B2
(45) Date of Patent: Aug. 8, 2006

(54) LIQUID CRYSTALLINE OXETANE COMPOUND, POLYMERIZABLE LIQUID CRYSTALLINE COMPOSITION, METHOD FOR PRODUCING LIQUID CRYSTAL FILM, OPTICAL FILM, AND LIQUID CRYSTAL DISPLAY

(75) Inventors: Takuya Matsumoto, Yokohama (JP); Hitoshi Mazaki, Yokohama (JP)

(73) Assignee: Nippon Oil Corporation, Tokyo (JP)

( * ) Notice: Subject to any disclaimer, the term of this patent is extended or adjusted under 35 U.S.C. 154(b) by 0 days.

(21) Appl. No.: 10/801,459

(22) Filed: Mar. 16, 2004

(65) Prior Publication Data

US 2004/0173773 A1 Sep. 9, 2004

Related U.S. Application Data

(63) Continuation of application No. PCT/JP02/09119, filed on Sep. 6, 2002.

(30) Foreign Application Priority Data

Sep. 20, 2001 (JP) ............................. 2001-286652

(51) Int. Cl.
  *C09K 19/38* (2006.01)
  *C09K 19/34* (2006.01)
  *C09K 19/20* (2006.01)

(52) U.S. Cl. .................. 428/1.1; 428/1.3; 252/299.01; 252/299.61; 252/299.67

(58) Field of Classification Search ................ 428/1.1, 428/1.3; 252/299.61, 299.01, 299.64, 299.65, 252/299.67; 528/271, 272, 417
See application file for complete search history.

(56) References Cited

U.S. PATENT DOCUMENTS

| | | | |
|---|---|---|---|
| 5,773,178 A | | 6/1998 | Shiota et al. |
| 6,139,772 A | * | 10/2000 | Ukon .................. 252/299.61 |
| 6,183,822 B1 | * | 2/2001 | Farrand et al. .............. 428/1.1 |
| 6,210,872 B1 | | 4/2001 | Hosaki et al. |
| 6,660,344 B1 | * | 12/2003 | Lub ........................ 428/1.1 |
| 6,666,989 B1 | * | 12/2003 | Toyne et al. .......... 252/299.01 |
| 6,894,141 B1 | * | 5/2005 | Satoh et al. ............... 528/196 |

FOREIGN PATENT DOCUMENTS

| | | |
|---|---|---|
| EP | 0 528 050 A1 | 2/1993 |
| EP | 0 896 047 A1 | 2/1999 |
| JP | 09-003454 A | 1/1997 |
| JP | 11-106380 * | 4/1999 |
| JP | 11-158258 A | 6/1999 |
| JP | 2003-213265 * | 7/2003 |
| WO | WO 02/28985 A1 | 4/2002 |

OTHER PUBLICATIONS

English translation by computer for JP 11-106380, http://www4.ipdl.jpo.go.jp/Tokujitu/PAJdetail.ipdl?N0000=60&N0120=01&N2001=2&N3001=H11-106380.*

* cited by examiner

*Primary Examiner*—Shean C Wu
(74) *Attorney, Agent, or Firm*—Akin Gump Strauss Hauer & Feld, LLP

(57) ABSTRACT

A novel liquid crystalline compound has the formula:

$$Z^1\text{-}(CH_2)_n\text{-}L^1\text{-}P^1\text{-}L^2\text{-}P^2\text{-}L^3\text{-}P^3\text{-}L^4\text{-}(CH_2)_m\text{-}Z^2 \quad (1)$$

wherein $Z^1$ and $Z^2$ are each independently a group represented by any one of formulas (2), (3) and (4) below, $L^1$, $L^2$, $L^3$, and $L^4$ each independently indicate direct bond or are a group represented by any of —O—, —O—CO—, or —CO—O—, $P^1$ and $P^2$ are each independently a group represented by formula (5) below, and $P^3$ indicates direct bond or is a group represented by formula (5) below, n and m are each independently an integer of 0 to 8;

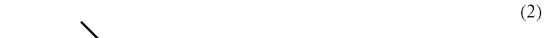

(2)

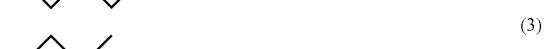

(3)

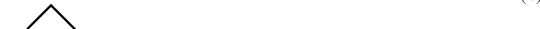

(4)

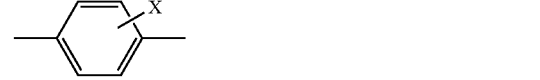

(5)

wherein X is selected from the group consisting of hydrogen, methyl, or halogen and provides an optical film with an excellent capability of retaining the aligned liquid crystal orientation which has been fixed and in mechanical strength.

4 Claims, 5 Drawing Sheets

LIQUID CRYSTALLINE OXETANE COMPOUND, POLYMERIZABLE LIQUID CRYSTALLINE COMPOSITION, METHOD FOR PRODUCING LIQUID CRYSTAL FILM, OPTICAL FILM, AND LIQUID CRYSTAL DISPLAY

CROSS-REFERENCE TO RELATED APPLICATIONS

This application is a continuation of International Application No. PCT/JP02/09119, filed Sep. 6, 2002, the disclosure of which is incorporated herein by reference.

BACKGROUND OF THE INVENTION

The present invention relates to a novel polymerizable liquid crystalline oxetane compound, a polymerizable liquid crystalline composition containing such a liquid crystalline oxetane compound, a method for producing a liquid crystal film using such a polymerizable liquid crystalline composition, an optical film comprising such a liquid crystal film produced by such a method, and a liquid crystal display equipped with such an optical film.

Active studies and developments have been carried out to utilize liquid crystalline compounds as optical materials, and many of them have been already put into practical use. In order to apply a liquid crystalline compound to an optical material, it is essential that after the compound is fixed in an aligned liquid crystal structure, it can be retained in the fixed aligned structure under practical use conditions. As methods for retaining the fixed aligned structure of a liquid crystalline compound, there have been proposed various methods wherein to use polymerizable liquid crystalline compounds, to use polymeric liquid crystalline compounds, and to use polymeric liquid crystalline compounds having crosslinkable reactive groups.

Japanese Patent Laid-Open Publication No. 11-080081 discloses a method using polymeric liquid crystalline compounds having crosslinkable reactive groups, such as those having a mesogen portion comprising two or more benzene rings or similar rings, spacer portions each comprising a hydrocarbon chain, and radically polymerizable reactive groups such as (meth)acrylate group at one or both of the terminal ends. In this method, a polymerizable liquid crystalline compound is coated in a heat-melted state or in the form of a solution on an alignment substrate to be formed into a liquid crystal layer and dried if necessary. Thereafter, the liquid crystal layer thus formed is aligned in a liquid crystal orientation by heating and then polymerized by photo-irradiation so as to fix the liquid crystal orientation. However, this method is required to suppress an undesired polymerization inhibition effect caused by oxygen in the air and also needs some complicated operations such as a photo-irradiation under an inert gas atmosphere and improved facilities and apparatus in connection with such complicated operations. Since (meth)acrylate group is easily polymerizable with light or heat, a careful attention must be paid during the synthesis.

As disclosed in Japanese Patent Laid-Open Publication No. 11-158258, there is a method using polymeric liquid crystalline compounds, such as liquid crystalline polyesters excellent in capability of retaining an aligned liquid crystal orientation. However, due to the wide-spread of mobile communication tools, optical films formed from liquid crystalline polyesters are demanded to have a retainability of the aligned structure under more sever conditions and to be more in excellent mechanical strength.

As methods using polymeric liquid crystalline compounds having polymerizable reactive groups, Japanese Patent Laid-Open Publication No. 9-3454 proposes a method wherein polymerizable reactive groups are introduced into the main chain of a polymer and a method wherein a monomer unit having polymerizable reactive groups are introduced into the side chain(s). However, since the liquid crystallinity of the compounds is reduced in either of the methods, there is a limit to introduce polymerizable reactive groups in such a large amount that the mechanical strength is sufficiently enhanced. Therefore, alternative methods have been demanded.

BRIEF SUMMARY OF THE INVENTION

The object of the present invention is to provide a liquid crystalline compound containing no functional group such as (meth)acrylate and epoxy groups, the syntheses of which are difficult. The present invention is also intended to provide a novel optical film which can be produced without employing complicated processes such as a photo-irradiation under an inert gas atmosphere due to the use of the aforesaid liquid crystalline compound and is excellent in a retainability of the aligned liquid crystal structure after the compound is aligned and fixed in a liquid crystal orientation and excellent in mechanical strength.

After an extensive research and study of a polymerizable liquid crystalline compound which is easy in synthesis and has an excellent alignability in a liquid crystal orientation, the inventors of the present invention found a polymerizable liquid crystalline compound having cationically polymerizable oxetane groups as polymerizable reactive groups. As a result, it was also found that when the aforesaid liquid crystalline compound is polymerized after it is aligned in a liquid crystal orientation, and formed into a film, a novel optical film can be developed which film has an excellent alignment retainability after the compound is aligned and fixed in the liquid crystal orientation and has an excellent mechanical strength.

That is, according to a first aspect of the present invention, there is provided a liquid crystalline oxetane compound represented by the formula:

$$Z^1\text{-}(CH_2)_n\text{-}L^1\text{-}P^1\text{-}L^2\text{-}P^2\text{-}L^3\text{-}P^3\text{-}L^4\text{-}(CH_2)_m\text{-}Z^2 \quad (1)$$

wherein $Z^1$ and $Z^2$ are each independently a group represented by any one of formulas (2), (3) and (4) below, $L^1$, $L^2$, $L^3$, and $L^4$ each independently indicate direct bond or are a group represented by any of —O—, —O—CO—, or —CO—O—, $P^1$ and $P^2$ are each independently a group represented by formula (5) below, and $P^3$ indicates direct bond or is a group represented by formula (5) below, n and m are each independently an integer of 0 to 8;

(2)

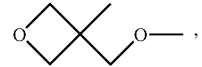
(3)

-continued

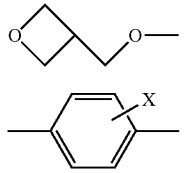
(4)

(5)

wherein X is selected from the group consisting of hydrogen, methyl, or halogen.

According to a second aspect of the present invention, there is provided the liquid crystalline oxetane compound of the first aspect wherein $Z^1$ and $Z^2$ are each independently a group represented by formula (2), $L^1$ and $L^4$ are each independently a group of —O—, $L^2$ is a group of —CO—O—, $L^3$ is a group of —O—CO—, $P^1$ and $P^3$ are each independently 1,4-phenylene group, and $P^2$ is 1,4-phenylene group or methyl-substituted 1,4-phenylene group.

According to a third aspect of the present invention, there is provided a polymerizable liquid crystalline composition containing at least 10 percent by mass or more of the liquid crystalline compound of the first aspect.

According to a forth aspect of the present invention, there is provided the polymerizable liquid crystalline composition of the third aspect containing a photo cation generator and/or a thermal cation generator.

According to a fifth aspect of the present invention, there is provided a method of producing a liquid crystal film wherein a layer of the polymerizable liquid crystalline composition of the third or forth aspect of the present invention is formed on an alignable film so as to be aligned in a liquid crystal orientation and then polymerized with light and/or heat to fix the aligned structure.

According to a sixth aspect of the present invention, there is provided an optical film comprising a liquid crystal film produced by the method of the fifth aspect.

According to a seventh aspect of the present invention, there is provided the optical film of the sixth aspect having a function as any one selected from a uniaxial or twisted retardation film, a cholesteric orientation-type circular polarizing reflection film, and a nematic hybrid orientation-type compensation film.

According to an eighth aspect of the present invention, there is provided a liquid crystal display equipped with at least one optical film of the six or seventh aspect.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
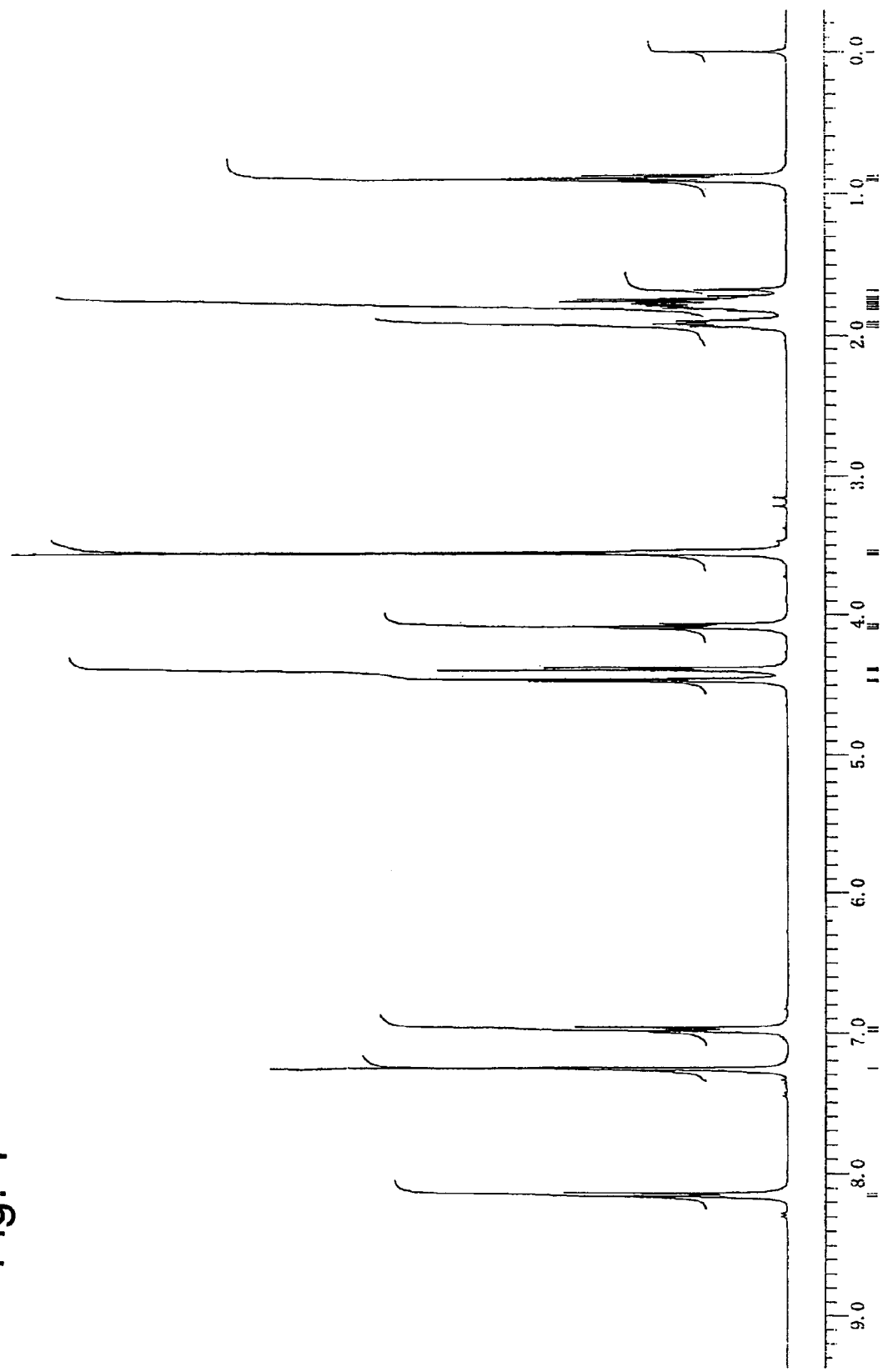
FIG. 1 is the NMR spectrum of liquid crystalline oxetane compound 1 synthesized in Example 1.

The liquid crystalline oxetane compounds of the present invention are those represented by the following formula:

$$Z^1\text{-}(CH_2)_n\text{-}L^1\text{-}P^1\text{-}L^2\text{-}P^2\text{-}L^3\text{-}P^3\text{-}L^4\text{-}(CH_2)_m\text{-}Z^2 \quad (1)$$

wherein $Z^1$ and $Z^2$ are each independently a group represented by any one of formulas (2), (3) and (4) below, $L^1$, $L^2$, $L^3$, and $L^4$ each independently indicate direct bond or are a group represented by any one of —O—, —O—CO—, or —CO—O—, $P^1$ and $P^2$ are each independently a group represented by formula (5) below, and $P^3$ indicates direct bond or is a group represented by formula (5) below, n and m are each independently an integer of 0 to 8;

(2)

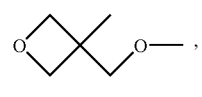
(3)

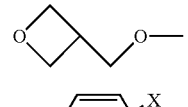
(4)

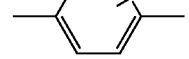
(5)

wherein X is selected from the group consisting of hydrogen, methyl, or halogen.

That is, the liquid crystalline oxetane compounds of the present invention are compounds containing a mesogen portion comprising an aromatic ester or the like, spacer portions each comprising mainly a hydrocarbon chain, and reactive oxetane groups located at the both terminal ends, as constitution units and exhibiting liquid crystallinity.

First of all, each of the constitution units are described.

In the present invention, the mesogen portion represented by "$L^1$-$P^1$-$L^2$-$P^2$-$L^3$-$P^3$-$L^4$-" of formula (1) has such a structure that two or three aromatic rings bond each other directly or via an ether bond or ester bond at the 1,4-position. The aromatic rings may be substituted by methyl or halogen such fluorine or chlorine.

In formula (1), $L^1$, $L^2$, $L^3$, and $L^4$ each independently indicate direct bond wherein the groups at both sides of any one of L groups bond to each other directly without via the L group, or are a group represented by any one of —O—, —O—CO— or —CO—O—, $P^1$ and $P^2$ are each independently a group represented by formula (5), and $P^3$ indicates direct bond wherein the groups ($L^3$ and $L^4$) at both sides of $P^3$ group bond to each other directly without via $P^3$ group or is a group represented by formula (5).

Specific examples of a group represented by formula (5) are 1,4-phenylene, methyl-substituted 1,4-phenylene, fluorine-substituted 1,4-phenylene, and chlorine-substituted 1,4-phenylene groups.

Specific examples of the mesogen portion of the liquid crystalline oxetane compounds of the present invention are those represented by the following formulas:

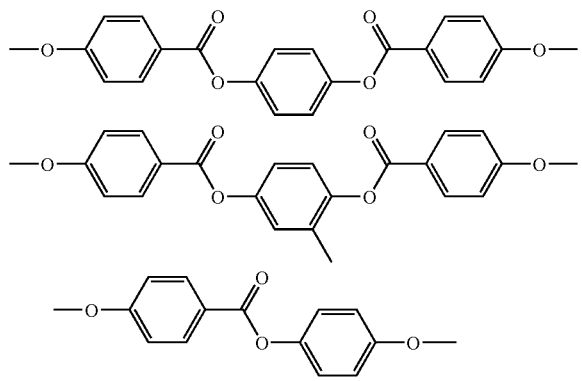

In the present invention, the spacer portions represented by "—(CH$_2$)$_n$—" and "—(CH$_2$)$_m$—" in formula (1) each independently indicate a direct bond wherein n or m is 0 or are a divalent straight-chain hydrocarbon group having 1 to 8 carbon atoms. If the intended compounds have liquid crystallinity, the mesogen portion may bond directly to the oxetane groups in the absence of the spacer portions, i.e., straight-chain hydrocarbon groups. In general, too short spacers would cause the narrowed temperature range at which liquid crystallinity is exhibited and too long spacers would deteriorate the heat resistance of the resulting film after it is cured. Therefore, the carbon number of each of the spacer portions is preferably 2 to 6.

With the objective of easy synthesis, the reactive oxetane portions are preferably any of those represented by the following formulas:

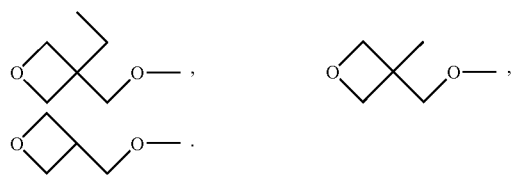

No particular limitation is imposed on the method of synthesizing the liquid crystalline oxetane compounds of the present invention. Therefore, there may be used any conventional method utilized in the field of organic chemistry. For example, the liquid crystalline oxetane compound may be synthesized by bonding oxetane portions to spacer portions by a method such as the Williamson ether synthesis and then bonding these bonded portions to a mesogen portion having been synthesized by an ester synthesis method using a condensation agent such as DCC (dicyclohexylcarbodiimide), by the same similar ester synthesis method. Alternatively, the liquid crystalline oxetane compound may be synthesized by bonding oxetane group portions to spacer portions and bonding thereto one aromatic ring having a carboxyl group by an ether synthesis and then ester-synthesized with hydroquinone.

During these syntheses, since the oxetane group portions at the both terminal ends have cationic polymerizability, it is necessary to select the reaction conditions with a consideration given to side reactions such as polymerization and ring-opening possibly occurring under strong acid conditions. The oxetane group has a less possibility of the occurrence of such side reactions, compared with epoxy group which is though a similar cationically polymerizable functional group. Furthermore, since the oxetane group may allow various compounds similar thereto, such as alcohols, phenols, and carboxylic acids to be reacted one after another, the use of protection groups may be considered if necessary. The crude liquid crystalline oxetane compound thus synthesized may be refined by recrystallization or column chromatography. Recrystallization is effective particularly for compounds of a high liquid crystallinity. Even if the compound can not be recrystallized at ordinary temperature, it may be able to be recrystallized after being cooled to a lower temperature of such as −20° C. The crude liquid crystalline oxetane compound thus obtained can be identified with an analyzing means such as $^1$H-NMR (nuclear magnetic resonance).

The liquid crystalline oxetane compounds of the present invention are preferably those represented by formula (1) wherein $Z^1$ and $Z^2$ are each independently a group represented by formula (2), $L^1$ and $L^4$ are each independently a group of —O—, $L^2$ is a group of —CO—O—, $L^3$ is a group of —O—CO—, $P^1$ and $P^3$ are each independently 1,4-phenylene group, and $P^2$ is 1,4-phenylene group or methyl-substituted 1,4-phenylene group.

Next, described are polymerizable liquid crystalline compositions containing a liquid crystalline oxetane compound of the present invention.

The polymerizable liquid crystalline compositions of the present invention are those containing at least 10 percent by mass or more, preferably 30 percent by mass or more of a liquid crystalline oxetane compound of the present invention. A composition containing less than 10 percent by mass of the liquid crystalline oxetane compound is too low in polymerizable group concentration and thus would be insufficient in mechanical strength after being polymerized.

The polymerizable liquid crystalline composition of the present invention comprises a liquid crystalline oxetane compound of the present invention and various compounds which can be blended therewith without hindering the liquid crystallinity of the oxetane compound.

Compounds which can be blended with the liquid crystalline oxetane compound are those bonding at least one oxetane group (excluding the liquid crystalline oxetane compounds of the present invention); those bonding at least one cationically polymerizable functional group other than oxetane group, such as epoxy and vinyl ether group; various polymeric compounds having a film forming ability; and various low molecular or polymeric liquid crystalline compounds exhibiting a nematic, cholesteric, or discotic liquid crystallinity. Various polymers having a film forming ability can be blended to an extent that the achievement of the purposes of the present invention is not bothered. Furthermore, various optical active compounds regardless whether they have liquid crystallinity or not can be blended for the purpose of allowing the polymerizable liquid crystalline compositions of the present invention to exhibit a cholesteric liquid crystallinity. Among these compounds, those bonding at least one cationically polymerizable functional group are preferred because they are copolymerizable with the liquid crystalline oxetane compound of the present invention constituting the polymerizable liquid crystalline composition upon polymerization thereof.

Next, described are photo cation generators and/or thermal cation generators (which may be referred to as "cation generators" in combination hereinafter) which may be contained in the polymerizable liquid crystalline composition.

Since the polymerizable liquid crystalline compositions of the present invention comprise a compound having cationically polymerizable oxetane groups of the present invention, it is preferred to add a cation generator for polymerizing the compound. Preferred cation generators are compounds capable of generating cations by applying an external stimulus such as light and/or heat, such as those having a trichloromethyl or quinonediazido group and organic sulfonium salt-, iodonium salt-, or phosphonium salt-based compounds. If necessary, various sensitizers may be used in combination.

In more detail, the term "photo cation generator" used herein denotes a compound which can generate cations by irradiating a light with a specific wavelength and may be organic sulfonium salt-, iodonium salt-, or phosphonium salt-based compounds. Counter ions of these compounds are preferably antimonate, phosphate, and borate. Specific examples are $Ar_3S^+SbF_6^-$, $Ar_3P^+BF_4^-$, and $Ar_2I^+PF_6^-$ wherein Ar indicates phenyl or substituted phenyl group. Sulfonic acid esters, triazines, diazomethanes, β-ketosulfone, iminosulfonate, and benzoinsulfonate can also be used.

The term "thermal cation generator" used herein denotes a compound which can generate cations by heating it to a certain temperature and may be benzylsulfonium salts, benzylammonium salts, benzylpyridinium salts, benzylphosphonium salts, hydradinium salts, carbonic acid esters, sulfonic acid esters, amineimides, antimony pentachloride-acetyl chloride complexes, diaryliodonium salt-dibenzyloxy copper, and halogenated boron-tertiary amine adducts.

Alternatively, there may be employed a method wherein a polymerizable liquid crystalline composition having been blended with a compound generating cations, such as Lewis acid is prepared and then the oxetane group is polymerized after or simultaneously with forming a liquid crystal orientation. However, in a practical manner, it is more preferred to use a cation generator eliciting the generation of cations with heat or light because both sufficient liquid crystal orientation and polymerization degree can be achieved more frequently in the case where a liquid crystal orientation aligning process and a polymerization process are separated.

In the case of using a thermal cation generator, a heat treatment for aligning the polymerizable liquid crystalline composition is conducted at a temperature lower than the activation temperature of the thermal cation generator which is usually a 50% dissociation temperature, followed by a step of generating cations wherein a heat treatment is conducted at the activation temperature or higher to dissociate the thermal cation generator thereby reacting the oxetane groups with the cations thus generated. This method has an advantage that the aligning process and polymerization reaction can be conducted only with a heat treatment facilities. However, this method has a disadvantage that since the aligning and polymerization processes are separated only with heat, i.e., difference in temperature, polymerization may slightly progress during the aligning process or may not progress sufficiently during the actual polymerization process.

In the case of using a photo cation generator, the polymerizable liquid crystalline composition can be aligned, maintaining sufficient fluidity without being polymerizing or decomposing during the aligning process if the heat treatment for aligning in a liquid crystal orientation is conducted under dark conditions where the photo cation generator is not dissociated. Thereafter, the polymerizable liquid crystalline composition may be allowed to polymerize, i.e., cure by irradiating a light from a light source capable of emitting an appropriate wavelength of light so as to generate cations.

Since the amount of the cation generators to be added in the polymerizable liquid crystalline composition varies depending on the structure of the mesogen portion or spacer portions constituting the liquid crystalline oxetane compound to be used, the equivalent weight of the oxetanyl group, and the conditions for aligning in a liquid crystal orientation, it can not be determined with certainty. However, it is within the range of usually 100 ppm by mass to 20 percent by mass, preferably 1000 ppm by mass to 10 percent by mass, more preferably 0.2 percent by mass to 7 percent by mass, and most preferably 0.5 percent by mass to 5 percent by mass in terms of the ratio to the liquid crystalline oxetane compound. A cation generator in an amount of less than 100 ppm by mass is not preferred because polymerization may not progress due to the insufficient amount of cation to be generated. A cation generator in an amount of more than 20 percent by mass of the cation generator is not also preferred because the liquid crystallinity of the polymerizable liquid crystalline composition would be reduced, resulting in a insufficient aligned liquid crystal orientation and in a large amount of the decomposed cation generator remains in the resulting liquid crystal film and thus deteriorates the light resistance thereof.

Among the above-described cation generators, the photo cation generators capable of generating cations with light are particularly preferred because they can generate cations and polymerize (cure) the polymerizable liquid crystalline composition at any temperature at which the composition exhibits a liquid crystal phase.

Next, described is a method of producing a liquid crystal film using a polymerizable liquid crystalline composition of the present invention. Although not restricted, the film producing method preferably goes through each of the steps included in the method described below.

A liquid crystal film made from a polymerizable liquid crystalline composition of the present invention may be in any form such as one wherein a liquid crystal film is kept on an alignment substrate, i.e., (alignment substrate/(alignment layer)/liquid crystal film); one wherein a liquid crystal film is transferred to a transparent substrate film other than an alignment substrate, i.e., (transparent substrate film/liquid crystal film); or one which is a single layer of a liquid crystal film when it has a self-standing property.

Examples of the alignment substrates which can be used in the present invention are films of such as polyimide, polyamide, polyamideimide, polyphenylene sulfide, polyphenylene oxide, polyether ketone, polyetherether ketone, polyether sulfone, polysulfone, polyethylene terephthalate, polyethylene naphthalate, polyarylate, triacetyl cellulose, epoxy resins, and phenol resins and uniaxially stretched films thereof. Some of these films exhibit a sufficient alignability for the polymerizable liquid crystalline composition of the present invention depending on the production method of the films even though they are not subjected to an aligning treatment. However, if a film does not have alignability sufficiently or at all, the film may be stretched by an appropriate heating treatment; subjected to a rubbing treatment wherein the film is rubbed in one direction with a rayon cloth or wherein the film is rubbed after a conventional alignment layer of polyimide, polyvinyl alcohol, or a silane coupling agent is formed over the film; an oblique vapor deposition with silicon oxide; or subjected to the combination of these treatments to be provided with alignability. Alternatively, the aligning substrate may be a metal plates of aluminum, iron, or copper and any of various glass plates on which surfaces fine grooves are regularly formed.

In the case where an alignment substrate is not optically isotropic or makes the resulting liquid crystal film opaque at a wavelength region where the film is intended to be used, the liquid crystal film may be transferred from such an alignment substrate to an optically isotropic film or a substrate which is transparent at a wavelength region where the liquid crystal film is intended to be used. The transferring method may be those as disclosed in Japanese Patent Laid-Open Publication Nos. 4-57017 and 5-333313 wherein after a liquid crystal film layer on an alignment substrate is laminated via a tacky adhesive or adhesive over a transparent substrate which is different from the alignment substrate and on which the liquid crystal film layer is to be transferred, facing the another substrate and if necessary the adhesive is cured, only the liquid crystal film is transferred to the another substrate by peeling off the alignment substrate from the laminate.

Examples of the transparent substrate onto which the liquid crystal layer is transferred include triacetyl cellulose films such as Fujitack (manufactured by Fuji Photo Film Co., Ltd.) and Konicatack (manufactured by Konica Corp.); a TPX film (manufactured by Mitsui Chemical Inc.); an Arton film (manufactured by JSR); a Zeonex film (manufactured by Nippon Zeon Co., Ltd.); and a Acryprene film (manufactured by Mitsubishi Rayon Co., Ltd.). If necessary, a polarizer may be used as a transparent film. Alternatively, a quartz plate or a glass may be used. A polarizer may be used regardless of whether or not a protective layer is used.

No particular limitation is imposed on the tacky adhesive or adhesive to be used to transfer the liquid crystal film as long as it is of optical grade. Therefore, there may be used conventional acrylic-, epoxy resin-, ethylene-vinyl acetate copolymer-, rubber-, urethane-based ones, mixture types thereof, or various reactive ones of such as thermal curing type and/or photo curing type or electron radiation curing types.

The reaction conditions under which the reactive tacky adhesives or adhesives are cured vary depending on its formulation, viscosity and reaction temperature thereof. Therefore, the curing may be conducted under the conditions properly selected. For example, photo-curing type adhesives may be cured at a similar irradiation dose using a similar light source to those used for a photo cation generator described hereinafter. Electron radiation curing type adhesives may be cured at an accelerating voltage of usually 25 kV to 200 kV and preferably 50 kV to 100 kV.

The liquid crystal film may be produced by a method wherein a polymerizable liquid crystalline composition in a molten state or in the form of a solution is coated over an alignment substrate. The coated layer on the alignment layer is dried, heated for aligning it in a liquid crystal orientation, and subjected to a photo irradiation and/or a heat treatment for polymerization thereby being formed into the liquid crystal film.

No particular limitation is imposed on the solvent used for preparing a solution of a polymerizable liquid crystalline composition of the present invention as long as it can dissolve the liquid crystalline oxetane compound or other components constituting the composition and be evaporated under appropriate conditions. Preferred examples of the solvent include ketones such as acetone, methyl ethyl ketone, and isophorone; ether alcohols such as butoxy ethyl alcohol, hexyloxy ethyl alcohol, and methoxy-2-propanol; glycol ethers such as ethylene glycol dimethylether and diethylene glycol dimethyl ether; ester-based solvents such as ethyl acetate, methoxypropyl acetate and ethyl lactate; phenol-based solvents such as phenol and chlorophenol; amide-based solvents such as N,N-dimethylformamide, N,N-dimethylacetoamide, and N-methylpyrrolidone; halogenated hydrocarbon-based solvents such as chloroform, tetrachloroethane, and dichlorobenzene; and mixtures thereof. Surfactants, defoaming agents, or leveling agents may be added to the solution so as to form a uniform film layer on an alignment substrate. Furthermore, for the purpose of coloring, dichroric dyes, dyes, or pigments may be added to an extent that the exhibition of liquid crystallinity is not bothered.

No particular limitation is imposed on the method of coating a polymerizable liquid crystalline composition of the present invention as long as it can ensure the uniformity of the film layer. Therefore, there may be used any conventional method such as roll coating, die coating, dip coating, curtain coating, or spin coating methods. The coating may be followed by a solvent-removing process, i.e., drying using a heater or a hot air blowing.

Thereafter, if necessary, a heat treatment is conducted so as to form a liquid crystal orientation, followed by polymerization (curing) by a photo irradiation and/or a heat treatment. In this heat treatment, the polymerizable liquid crystalline composition used is heated to the range of temperatures at which the composition exhibits a liquid crystal phase, so as to align the composition in the liquid crystal orientation by its self-alignability. Since the conditions for the heat treatment vary in optimum conditions and limits depending on the liquid crystal phase behavior temperature (transition temperature) of the polymerizable liquid crystalline composition to be used, it can not be determined with certainty. However, the heat treatment is conducted at a temperature within the range of usually 10 to 200° C., preferably 20 to 150° C. Temperatures below 10° C. are not preferred because there is a possibility that the composition may not be aligned in a liquid crystal orientation sufficiently, while those in excess of 200° C. are not also preferred because the oxetane group and the substrate may be adversely affected. The heat treatment is conducted for usually 3 seconds to 30 minutes, preferably 10 seconds to 10 minutes. The heat treatment for shorter than 3 seconds is not preferred, because there is a possibility that the composition may not be aligned in a liquid crystal phase completely. Whereas, the heat treatment for longer than 30 minutes is not also preferred, because the productivity is extremely deteriorated. After the liquid crystalline composition is completely aligned in a liquid crystal orientation by the heat treatment or the like, the composition on the alignment substrate is cured by polymerization. In the present invention, the polymerization/curing process is conducted so as to modify the polymerizable liquid crystalline composition to be a harder film layer by fixing the completely aligned liquid crystal orientation.

Since the polymerizable liquid crystalline compositions of the present invention are cationically polymerizable, it is preferred to use suitable cation generators prior for polymerization/curing. These cation generators and method for using the same are as already described with respect to the above-described polymerizable liquid crystalline composition.

When a photo cation generator is used, it may be irradiated with a light from a light source capable of emitting an appropriate wavelength of light so as to be allowed to generate cations. A method of irradiating a light varies in optimum values of irradiation wavelength and strength and irradiation time, depending on the type or amount of a photo cation generator to be used. However, the light irradiation is generally conducted by irradiating a light from a light source having a spectrum near the absorption wavelength of a photo cation generator to be used, such as a metal halide lamp, a high-pressure mercury lamp, a low-pressure mercury lamp, a xenon lamp, an arc discharge lamp, a laser, and a synchrotorn radiation light source so as to decompose the photo cation generator. The irradiation dose per $cm^2$ is within the range of generally 1 to 2,000 mJ and preferably 10 to 1,000 mJ in the integrated irradiation dose. However, when the absorption region of a photo cation generator is extremely different from the spectrum of a light source or the polymerizable liquid crystalline composition itself can absorb a light in the wavelength of the light source, the irradiation dose is not limited to the above range. In these cases, a method may be employed in which a suitable photo sensitizer or two or more kinds of photo cation generators having different absorption wavelengths from each other are used.

The liquid crystalline composition layer (liquid crystal film) produced through the above-described processes becomes a sufficiently solid and strong film. More specifically, since the three-dimensional bond of the mesogen portion is achieved by the above-described curing reaction, the polymerizable liquid crystalline composition is improved not only in heat-resistance (the upper limit temperature at which the liquid crystal orientation is maintained) but also significantly improved in mechanical strength such as resistance to scratch, wear and cracking, compared with the composition prior to cure. The present invention is of great significance in the industrial sense because it can achieve the directly-opposed purposes, i.e., the accurate control of a liquid crystal orientation and an improvement in thermal/mechanical strength, at the same time.

The proper selection of compounds to be blended with the polymerizable liquid crystalline composition comprising the liquid crystalline oxetane compound of the present invention enables to control the aligned structure and enables to produce an optical film wherein a nematic orientation, a twisted nematic orientation, a cholesteric orientation, or a nematic hybrid orientation is fixed. The optical film has various applications depending on the aligned structure.

Among these films, those wherein a nematic or twisted nematic orientation is fixed function as optical retardation films and can be used as compensation plates for an STN-, TN-, OCB-, or HAN-transmission or reflection type liquid crystal display. Optical films wherein a cholesteric orientation is fixed can be used as polarizing reflective films for luminance enhancement, reflection color filters, and various decoration films utilizing color variations of reflection light depending on viewing angles due to the selective reflection. Those wherein a nematic hybrid orientation is fixed can be used as optical retardation films or wave plates utilizing a retardation upon viewing from the front and a viewing angle improving film for TN-type liquid crystal displays utilizing the asymmetric nature of viewing angle dependency of retardation. Furthermore, those having a function as a ¼ wavelength plate in combination with a polarizer can be used as anti-glare filters for reflection type liquid crystal displays and EL displays.

The present invention will be further described with reference to the following examples, but the present invention should not be construed as being limited thereto.

The analyzing methods used in the examples are as follows:

(1) $^1$H-NMR Measurement

A compound was dissolved in deuterated chloroform and measured by means of $^1$H-NMR at 400 MHz (JNM-GX400 manufactured by Nippon Electronics Co., Ltd.).

(2) Observation of Phase Behavior

A liquid crystal phase behavior was observed using an Olympus BH2 polarizing microscope while heating a sample on a Mettler hot stage.

A phase transition temperature was measured using a differential scanning calorimeter DSC7 manufactured by Perkin Elmer Co.

In the description of phase behaviors, "C" indicates crystal phase, "Nm" indicates nematic phase, and "Iso" indicates isotropic liquid phase.

(3) Parameter Measurement of Liquid Crystal Film

The retardation of a nematic orientation was measured using KOBRA-20ADH manufactured by Oji Keisokukiki Co., Ltd.

The twisted angle and retardation of a twisted nematic structure were measured using Optipro manufactured by SHINTECH, Inc.

EXAMPLE 1

Synthesis of Liquid Crystalline Oxetane Compound 1

Into a 2 L egg plant type flask were charged 46.3 g (0.40 mol) of 3-hydroxymethyl-3-ethyloxetane (product name: OXT-101 manufactured by Toagosei Co., Ltd.), 250.3 g (1.16 mol) of 1,4-dibromobutane (reagent, manufactured by Tokyo Kasei Kogyo Co., Ltd.), and 275 ml of hexane. 500 ml of a 33% sodium hydroxide aqueous solution containing 2 g of tetra-n-butylammonium bromide (reagent, manufactured by Tokyo Kasei Kogyo Co., Ltd.) was added to the mixture and vigorously stirred for 5 hours. After the mixture was refluxed at a temperature of 80° C. for one hour, 500 ml of deionized water was added thereto so as to separate the mixture into an organic phase and an aqueous phase. The aqueous phase was extracted three times with 160 ml of hexane. After the organic phase and the extracted phase were dried over magnesium sulfate, the solvent was distilled out in a vacuum. The resulting transparent liquid was distilled in a vacuum thereby obtaining 44.5 g (0.18 mol) of 3-[(4-bromobutoxy)methyl]-3-ethyloxetane as a distillate at 109° C./532 Pa (yield: 44%, identified with $^1$H-NMR).

In a 300 ml three neck flask, 5.2 g (31 mmol) of ethyl p-hydroxybenzoate, 4.7 g (34 mmol) of potassium carbonate anhydride, and 7.8 g (31 mmol) of the 3-[(4-bromobutoxy)methyl]-3-ethyloxetane were dissolved in 50 ml of dimethylformamide. After the solution remained turbid was heated to a temperature of 80° C. and stirred for 4 hours, the solvent was completely distilled out in a vacuum. To the resulting yellow oily substance were added 15 ml of a 7% sodium hydroxide aqueous solution and 15 ml of methanol. The mixture was refluxed for two and half hours. 1 N (normality) of hydrochloric acid was added to the mixture such that the pH is adjusted to about 3. The resulting white precipitate was filtered and dried in a vacuum thereby obtaining 8.6 g (28 mmol) of 4-[7-(3-ethyl-3-oxetanyl)-1,6-dioxaheptyl]benzoic acid (yield: 89%, identified with ¹H-NMR). The resulting compound was no more purified and used in the following reaction.

Into a 100 ml three neck flask were charged 1.1 g (9.6 mmol) of methanesulfonyl chloride, 0.1 g of nitrobenzene, and 10 ml of tetrahydrofuran. To the mixture was added a solution obtained by dissolving 3.1 g (10 mmol) of the 4-[7-(3-ethyl-3-oxetanyl)-1,6-dioxaheptyl]benzoic acid in 1.3 g (10 mmol) of diisopropylethylamine and 10 ml of tetrahydrofuran, while the mixture was cooled with ice. The mixture was stirred for 2 hours after the temperature thereof had been returned to ordinary temperature. To the mixture were added a solution obtained by dissolving 0.54 g (4.8 mmol) of hydroquinone in 8 ml of tetrahydrofuran, 0.3 g of dimethylaminopyridine, and 1.0 g of triethylamine. The mixture was refluxed for 3 hours. After the mixture was cooled, the resulting white precipitate was recrystallized from methanol thereby obtaining 1.9 g (2.8 mmol) of the intended liquid crystalline oxetane compound 1 represented by the following formula (yield: 55%, identified with ¹H-NMR).

Liquid Crystalline Oxetane Compound 1 a solution obtained by dissolving 3.1 g (10 mmol) of the 4-[7-(3-ethyl-3-oxetanyl)-1,6-dioxaheptyl]benzoic acid in 1.3 g (10 mmol) of diisopropylethylamine and 10 ml of tetrahydrofuran, while the mixture was cooled with ice. The mixture was stirred for 2 hours after the temperature thereof was returned to ordinary temperature. To the mixture were added a solution obtained by dissolving 0.6 g (4.8 mmol) of methylhydroquinone in 8 ml of tetrahydrofuran, 0.3 g of dimethylaminopyridine, and 1.0 g of triethylamine. The mixture was refluxed for 3 hours. After the mixture was cooled, 20 ml of a saturated sodium chloride solution and 50 ml of methylene chloride were added so as to separate the mixture into an organic phase and an aqueous phase. The aqueous phase was extracted twice with 20 ml of methylene chloride. After the organic phase and the extracted phase were dried over magnesium sulfate anhydride, the solvent was distilled out in a vacuum thereby obtaining a transparent oily product. The resulting oily product was purified with a silica gel chromatography using a mixed solvent of hexane-ethyl acetate (hexane:ethyl acetate=2:1 by volume ratio) as a mobile phase thereby obtaining 2.8 g (4.0 mmol) of

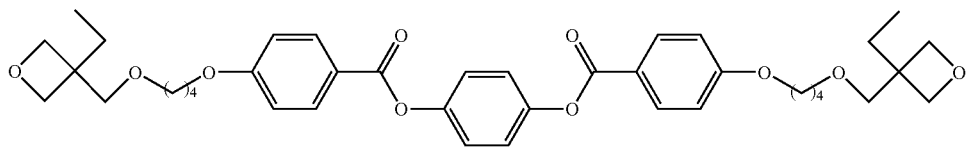

The ¹H-NMR spectrum of the resulting liquid crystalline oxetane compound 1 is shown in FIG. 1. The phase behavior and phase transition temperature of the resulting liquid crystalline oxetane compound were as follows:

[Liquid crystal phase behavior and phase transition temperature]

C—65° C.—Nm—94° C.—Iso theintended liquid crystalline oxetane compound 2 represented by the following formula (yield: 83%, identified with ¹H-NMR).

Liquid Crystalline Oxetane Compound 2

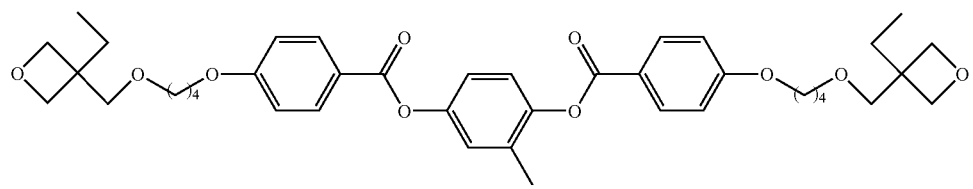

EXAMPLE 2

Synthesis of Liquid Crystalline Oxetane Compound 2

The procedure of Example 1 was repeated thereby synthesizing crude 4-[7-(3-ethyl-3-oxetanyl)-1,6-dioxaheptyl] benzoic acid. Into a 100 ml three neck flask were charged 1.1 g (9.6 mmol) of methanesulfonyl chloride, 0.1 g of nitrobenzene, and 10 ml of tetrahydrofuran, followed by addition of

EXAMPLE 3

Synthesis of Liquid Crystalline Oxetane Compound 3

Into a 300 ml three neck flask were charged 25.4 g of 2,3-dihydropyran (reagent, manufactured by Tokyo Kasei Kogyo Co., Ltd.), 41.4 g of p-hydroxybenzoic acid (reagent, manufactured by Tokyo Kasei Kogyo Co., Ltd.), and 3.7 g of pyridinium p-toluenesulfonate (reagent, manufactured by Tokyo Kasei Kogyo Co., Ltd.). The mixture was dissolved after addition of 20 ml of methylene chloride and 80 ml of absolute ether. After the mixture was vigorously stirred for about 3 hours, it was extracted 3 times with 70 ml of a 10% sodium hydroxide aqueous solution. The resulting extracted solution was neutralized with 1 N of hydrochloric acid until the pH is made to 6. The resulting precipitate was filtered and dried in a vacuum thereby obtaining 57.4 g of crude p-tetrahydropyranyloxy benzoic acid.

Into a 500 ml three neck flask equipped with a mechanical stirrer, a dropping funnel, and a Dimroth condenser were charged 5.73 g of methanesulfonyl chloride, 0.6 g of nitrobenzene, and 20 g of tetrahydrofuran. To the mixture was added a solution obtained by dissolving 11.1 g of the crude p-tetrahydropyranyloxy benzoic acid in 6.46 g disopropylethylamine and 50 g of tetrahydrofuran through the dropping funnel while the mixture was cooled with ice. After the mixture was stirred for one hour while cooled with ice, to the mixture while cooled with ice was added a solution obtained by dissolving 12.2 g of p-octyloxyphenol (reagent manufactured by Kanto Kagaku) in 6.67 g of triethylamine and 50 g of tetrahydrofuran. The mixture was refluxed for one hour. The reaction solution was cooled and then extracted with diethylether. After the organic phase was washed 3 times with 1 N of hydrochloric acid and once with a sodium chloride solution, the solvent was distilled out in a vacuum. To the resulting oily product were added 20 ml of tetrahydrofuran and 20 ml of 1 N of hydrochloric acid. The mixture was refluxed for one hour. 50 ml of methylene chloride was added to the resulting reaction solution so as to separate the organic phase therefrom. After the organic phase was washed with 1 N of hydrochloric acid and a sodium chloride aqueous solution and then dried over magnesium sulfate anhydride, it was filtered. The solvent was distilled out in a vacuum. The resulting crude p-hydroxybenzoic acid-p-octyloxyphenol ester was recrystallized from ethylacetate/hexane thereby obtaining 5.13 g of crude p-hydroxybenzoic acid-p-octyloxyphenol ester. The resulting compound was identified with $^1$H-NMR.

Into a 200 ml three neck flask equipped with a dropping funnel and a Dimroth condenser were charged 20 g of 3-ethyl-3-hydroxymethyl-oxetane (product name: OXT-101 manufactured by Toagosei Co., Ltd.), 17.4 g of triethylamine, and 50 ml of diethylether. The mixture was cooled in an ice bath. 25 ml of a solution obtained by dissolving 19.7 g of methanesulfonyl chloride in diethylether was slowly added to the mixture through the dropping funnel. After the ice bath was removed and the mixture was stirred for one hour, the precipitated amine salt was filtered out. The remaining reaction solution was concentrated in a vacuum thereby obtaining crude mesilate.

Into a 200 ml three neck flask equipped with a mechanical stirrer and a Dimroth condenser was charged the crude mesilate and were added thereto 23.8 g of p-hydroxybenzoic acid ethyl ester (reagent, manufactured by Tokyo Kasei Kogyo Co., Ltd.) and 29.7 g of potassium carbonate (first grade reagent manufactured by Wako Pure Chemical Industries, Ltd). Lastly, dimethylformamide was added such that the total amount was made 180 ml. The mixture was heated to a temperature of 100° C. and stirred with the mechanical stirrer for 4 hours. After the mixture was then cooled to room temperature and the precipitated salt was filtered out, the solvent was distilled out in a vacuum therefrom and dried in a vacuum thereby obtaining a crude ester compound.

Into a 200 ml egg plant type flask equipped with a Dimroth condenser were charged the crude ester compound and 50 ml (61.4 g) of a 18.5% potassium hydroxide aqueous solution. The mixture was refluxed for 3 hours. The resulting reaction solution was poured into 700 ml of ice water in a 2 L beaker so as to be made a transparent solution. The solution was added with stirred to 40 ml (65.8 g) of a 39% sodium hydrogen sulfate aqueous solution. As a result, deposit was precipitated and thus filtered thereby obtaining crude p-(3-ethyl-3-oxetanyl)-methoxybenzoic acid. The resulting crude crystal was recrystallized from water/acetonitrile and dried in a vacuum thereby obtaining 29.3 g of p-(3-ethyl-3-oxetanyl)-methoxybenzoic acid.

Figure 2:
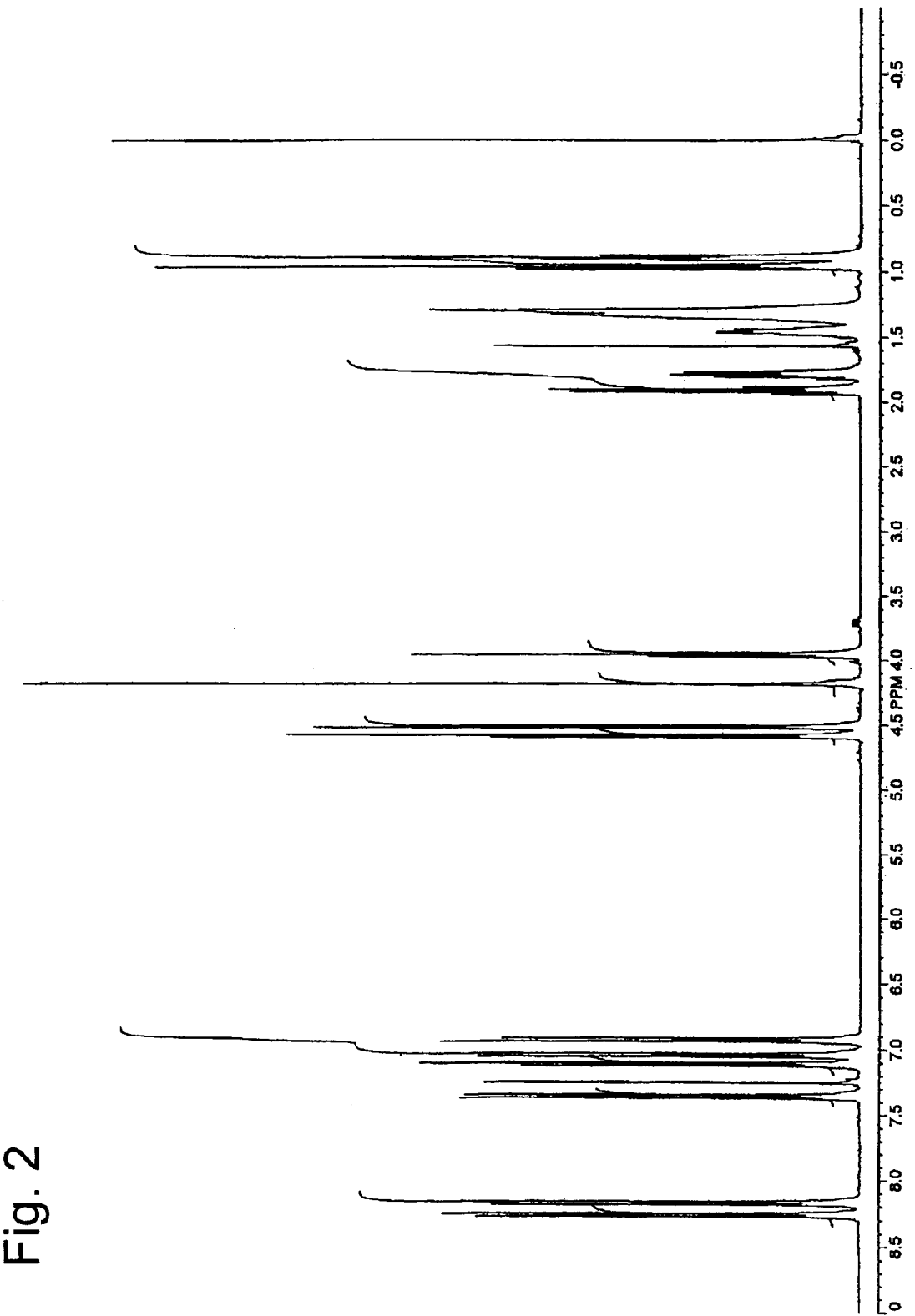
FIG. 2 is the NMR spectrum of liquid crystalline oxetane compound 3 synthesized in Example 3.

Into a 200 ml three neck flask equipped with a mechanical stirrer, a dropping funnel, and a Dimroth condenser were charged 1.72 g of methanesulfonyl chloride, 0.2 g of nitrobenzene, and 10 ml of tetrahydrofuran. The mixture was cooled in an ice bath. After through the dropping funnel was added slowly a solution obtained by dissolving 3.54 g of the p-(3-ethyl-3-oxetanyl)-methoxybenzoic acid in 1.94 g of diisopropylethylamine and 20 ml of tetrahydrofuran, the ice bath was removed. The mixture was stirred for one hour. To the mixture was further added a solution obtained by dissolving 5.13 g of the crude p-hydroxybenzoic acid-p-octyloxyphenol ester in 1.82 g of triethylamine and 20 ml of tetrahydrofuran. The mixture was stirred at a temperature of 70° C. for one hour. The resulting reaction solution was cooled and separated by adding 1 N of hydrochloric acid and diethylether. The organic phase was washed 3 times with a sodium chloride aqueous solution, dried over magnesium sulfate, and filtered. The solvent was distilled out in a vacuum thereby obtaining a white solid. The resulting solid was recrystallized from ethyl acetate/methanol and dried in a vacuum thereby obtaining 6.1 g of liquid crystalline oxetane compound 3 with a structure represented by the formula below. The $^1$H-NMR spectrum of the liquid crystalline oxetane compound 3 is shown in FIG. 2. The phase behavior and phase transition temperature of the compound 3 were as follows.

Liquid Crystalline Oxetane Compound 3

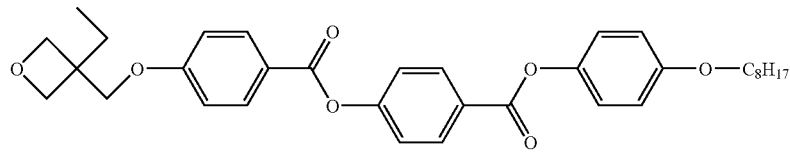

[Liquid crystal phase behavior and phase transition temperature]
C—98° C.—Nm—137° C.—Iso

EXAMPLE 4

Preparation of Polymerizable Liquid Crystalline Composition 4

1.0 g of liquid crystalline compound 1 and 1.0 g of liquid crystalline compound 3 synthesized in Examples 1 and 3, respectively were dissolved in 10 ml of methylene chloride and made homogeneous. The solvent was distilled out in a vacuum thereby obtaining polymerizable liquid crystalline composition 4. The phase behavior and phase transition temperature of the resulting composition 4 were as follows.
[Liquid crystal phase behavior and phase transition temperature]
C—46° C.—Nm—82° C.—Iso

EXAMPLE 5

Production of a Liquid Crystal Film Using Liquid Crystalline Oxetane Compound 1)

0.25 g of liquid crystalline oxetane compound 1 synthesized in Example 1 was dissolved in 2.5 ml of cyclohexanone and to the solution was added in a dark place 0.02 g of a propylene carbonate solution with 50% triarylsulfoniumhexafluoroantimonate (a reagent manufactured by Aldrich Co.). The insolubles were filtered with a polytetrafluoroethylene filter having a pore size of 0.45 μm thereby preparing a solution of a polymerizable liquid crystalline composition.

The resulting solution was spin-coated over a 50 μm thickness polyethylene terephthalate (PET) film (product name: T-60 manufactured by Toray Industries, Inc.) whose surface had been subjected to a rubbing treatment with a rayon cloth and then dried at a temperature of 60° C. on a hot plate. The resulting polymerizable liquid crystalline composition layer on the film was irradiated with an ultraviolet light in an integrated irradiation dose of 450 mJ/cm² from a high-pressure mercury lamp under an air atmosphere while being heated at a temperature of 75° C. and then cooled thereby obtaining a cured liquid crystalline composition layer (liquid crystal film).

Since the polyethylene terephthalate film used as a substrate is large in birefringence and thus not preferable for use in an optical film, the resulting film (the liquid crystalline composition layer) was transferred via an ultraviolet curing-type adhesive (product name: UV-3400 manufactured by Toagosei Co., Ltd.) onto a triacetylcellulose (TAC) film thereby obtaining optical film A. More specifically, a UV-3400 adhesive with a thickness of 5 μm was coated over the cured liquid crystalline composition layer on the PET film and laminated with a TAC film. After the laminate was subjected to an irradiation of ultraviolet light of 400 mJ/cm² from the TAC film side so as to cure the adhesive, the PET film was peeled off thereby obtaining optical film A.

As a result of observations of the resulting optical film A through a polarizing microscope, it was confirmed that it exhibited a monodomain uniform nematic liquid crystal orientation without the occurrence of disclination, and the retardation (product of birefringence and liquid crystalline composition layer thickness) was 115 nm. Thereafter, only the liquid crystalline composition layer portion was scrapped off and the glass transition temperature thereof was measured using a DSC. As a result, it was found to be 105° C. The pencil hardness of the liquid crystalline composition layer surface of optical film A was on the order of 2H, and thus it was confirmed that the layer had a sufficient hardness. As described above, it was confirmed that the use of liquid crystalline oxetane compound 1 enables to produce a film which is excellent in an alignability in a liquid crystal orientation, thermal stability and strength after being fixed in the liquid crystal orientation.

EXAMPLE 6

Production of a Liquid Crystal Film Using Polymerizable Liquid Crystalline Composition 4)

0.25 g of polymerizable liquid crystalline composition 4 synthesized in Example 4 was dissolved in 2.5 ml of triethylene glycol dimethylether. To the solution was added in a dark place 0.02 g of a propylene carbonate solution with 50% triarylsulfoniumhexafluoroantimonate (a reagent manufactured by Aldrich Co.). The insolubles were filtered with a polytetrafluoroethylene filter having a pore size of 0.45 μm thereby preparing a solution of a polymerizable liquid crystalline composition.

Figure 4:
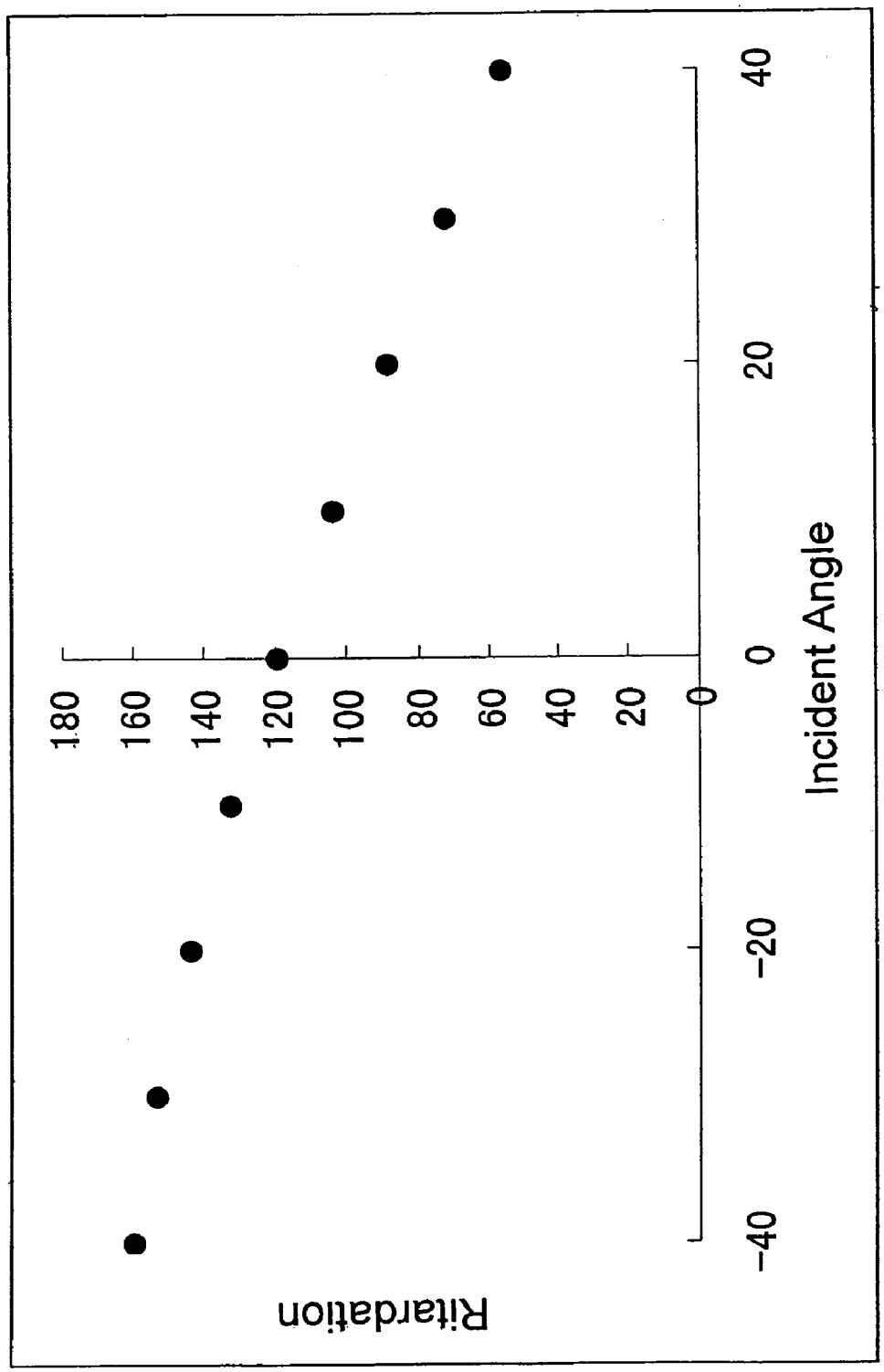
FIG. 4 shows the result of the retardation measurement conducted in Example 6.
Figure 5:
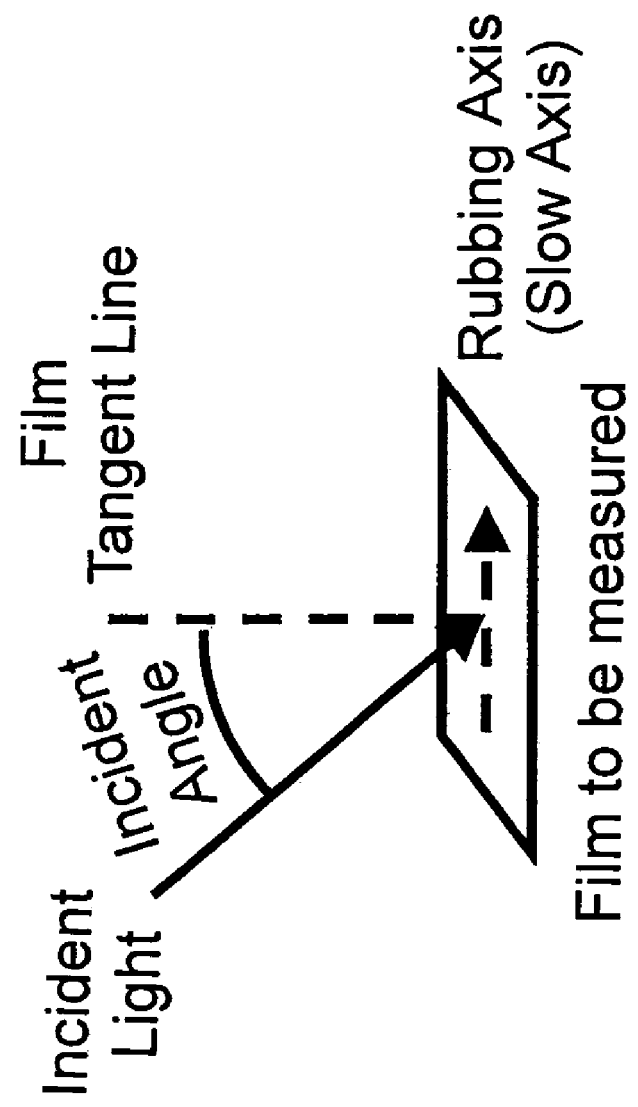
FIG. 5 shows the arrangement of the components used in the retardation measurement conducted in Example 6.

The procedure of Example 5 was repeated using the resulting solution thereby obtaining optical film C. As a result of observations of the resulting optical film C through a polarizing microscope, it was confirmed that it exhibited a monodomain uniform nematic liquid crystal orientation without the occurrence of disclination. When optical film C was viewed from the front, it had a retardation of 120 nm, as observed similarly in a uniaxial nematic orientation. However, when optical film C was viewed obliquely along the rubbing direction, the apparent retardation varied depending on the tilt direction of the film. It was thus found that the liquid crystalline composition layer had a hybrid orientation wherein the tilt direction thereof changed in the thickness direction. With the arrangement shown in FIG. 5, the retardation was measured using KOBRA-20AH. The result was shown in FIG. 4. Thereafter, only the liquid crystalline composition layer portion was scrapped off and the glass transition temperature thereof was measured using a DSC. As a result, it was found to be 100° C. The pencil hardness of the liquid crystalline composition layer surface of optical film C was on the order of 2H, and thus it was confirmed that the layer had a sufficient hardness. As described above, it was confirmed that the use of polymerizable liquid crystalline composition 4 enables to produce a film aligned in a hybrid orientation which is excellent in an alignability in a liquid crystal orientation and in thermal stability and strength after being fixed in the liquid crystal orientation.

COMPARATIVE EXAMPLE 1

Production of a Liquid Crystal Film Using Liquid Crystalline Acrylate Compound 5)

The production of an optical film was attempted by repeating the procedure of Example 5 except that liquid crystalline acrylate compound 5 having a structure represented by the formula below and synthesized in accordance with a method described in "Makromol. Chem., 190, 2255–2268 (1989)" was used instead of liquid crystalline oxetane compound 1 and a photo-polymerization initiator (product name: Irgacure 651 manufactured by Ciba-Geigy Limited) was used instead of a propylene carbonate solution with 50% triarylsulfoniumhexafluoroantimonate (a reagent manufactured by Aldrich Co.).

Liquid Crystalline Acrylate Compound 5

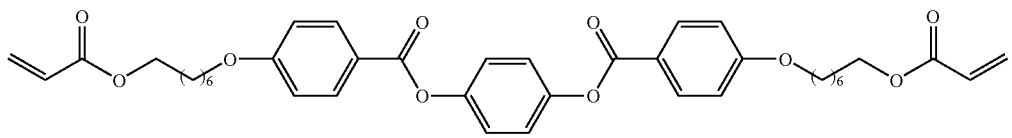

It seemed that the cure of the liquid crystalline composition did not progress even after it was irradiated with an ultraviolet light in an integrated irradiation dose of 450 mJ/cm$^2$ from a high-pressure mercury lamp under an air atmosphere. A film with sufficient mechanical strength was not able to be obtained.

EXAMPLE 7

Figure 3:
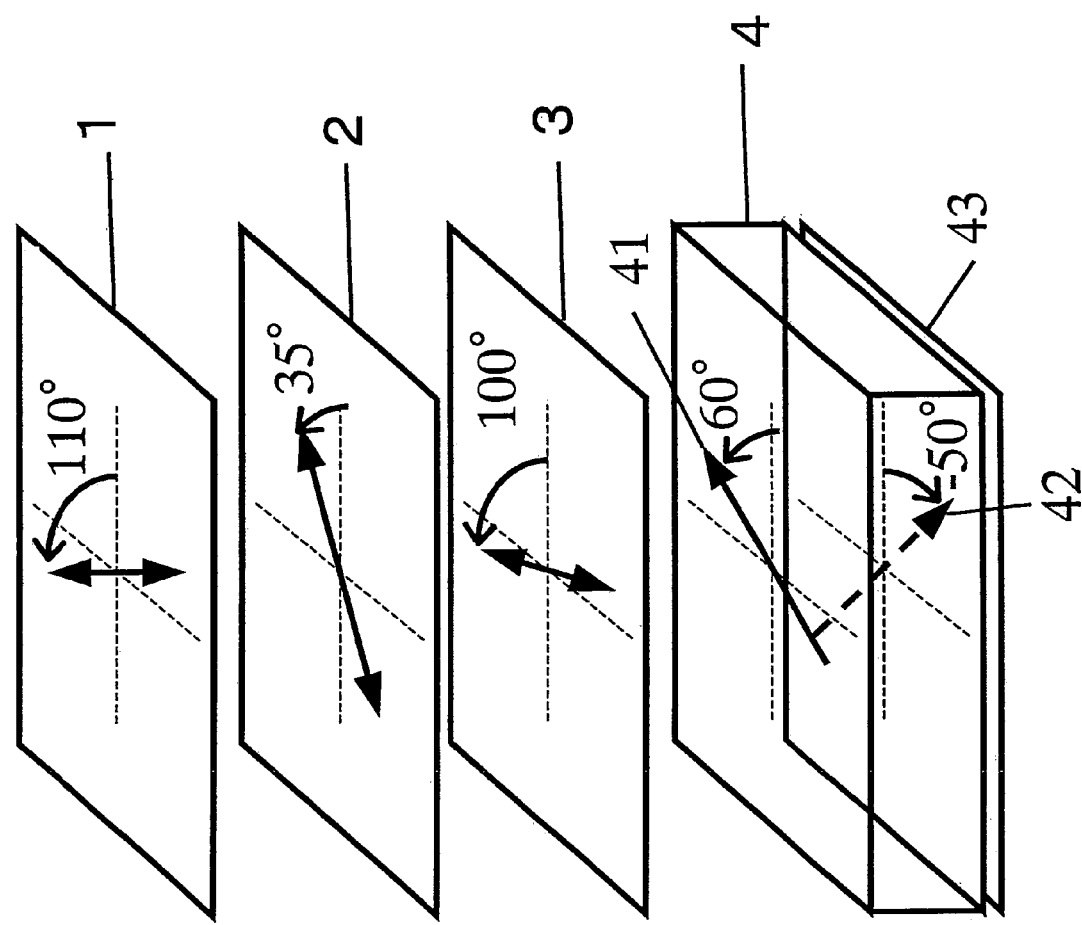
FIG. 3 is a perspective view of the liquid crystal display device used in Example 7, also showing the arrangement of each axis.

Optical film A with a retardation of 115 nm produced in Example 5 and optical film B with a retardation of 265 nm obtained by the same procedure of Example 5 except that thickness of the liquid crystalline composition layer was changed, were laminated using a non-carrier tacky adhesive such that the slow axis formed an angle of 65° thereby obtaining a wide bandwidth λ/4 plate. A polarizer 1 and a TFF-TN type liquid crystal cell 4 including the wide bandwidth λ/4 plate 2 (optical film B), a polarizer 3 (optical film A), and a reflector 43 were combined thereby producing a liquid crystal display with the arrangement shown in FIG. 3. In FIG. 3, the double-arrows of polarizer 1 indicates the absorption direction, the double-arrow of optical film B indicates the slow axis direction (rubbing direction), the double-arrows of optical film A indicates the slow axis direction (rubbing direction), the numeral 41 indicates the upper rubbing direction of the TN cell 4, and the numeral 42 indicates the lower rubbing direction of the TN cell 4. As a result, it was confirmed that contrast ratio (CR)=8, i.e., an excellent white and black image was obtained. The viewing angle of the display has no significant difference over that of a liquid crystal display having a wide bandwidth λ/4 plate comprising an Arton film (manufactured by JSR) which has been conventionally used. High contrast image was not able to be obtained when the optical films A and B were not used even though in whichever rest of the components were arranged.

APPLICABILITIES OF THE INDUSTRY

The liquid crystalline oxetane compound and polymerizable liquid crystalline composition containing the same of the present invention are excellent in alignability. Liquid crystal films and optical films obtained by curing a liquid crystalline compositions of the present invention are high in heat resistance (glass transition point) and hardness and excellent in mechanical strength and thus useful as retardation films for various liquid crystal displays.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:
1. A method of producing a liquid crystal film, the method comprising:
(a) forming a layer of a polymerizable liquid crystalline composition on an alignable film in an aligned liquid crystal orientation; and
(b) polymerizing the layer such that the aligned orientation is fixed;
wherein the polymerizable liquid crystalline composition comprises an oxetane compound represented by the formula

$$Z^1\text{-}(CH_2)_n\text{-}L^1\text{-}P^1\text{-}L^2\text{-}P^2\text{-}L^3\text{-}P^3\text{-}L^4\text{-}(CH_2)_m\text{-}Z^2 \quad (1)$$

wherein $Z^1$ and $Z^2$ are each independently a group represented by any one of formulas (2), (3) and (4) below, $L^1$, $L^2$, $L^3$, and $L^4$ each independently indicate direct bond or are a group represented by any of —O—, —O—CO—, or —CO—O—, P¹ and P² are each independently a group represented by formula (5) below, and P³ indicates direct bond or is a group represented by formula (5) below, n and m are each independently an integer of 2 to 6;

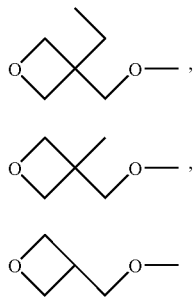

(2)

(3)

(4)

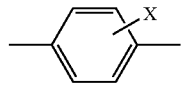

(5)

wherein X is selected from the group consisting of hydrogen, methyl, or halogen.

2. The method according to claim 1, wherein $Z^1$ and $Z^2$ each represent a group corresponding to the general formula (2), $L^1$ and $L^4$ each represent —O—, $L^2$ represents —CO—O—, $L^3$ represents —O—CO—, $P^1$ and $P^3$ each represent a 1,4-phenylene group, and $P^2$ represents a 1,4-phenylene group or a methyl-substituted 1,4-phenylene group.

3. The method according to claim 1, wherein the oxetane compound is present in the polymerizable liquid crystalline composition in an amount of at least 10% by mass.

4. The method according to claim 1, wherein the polymerizable liquid crystalline composition further comprises a photo cation generator and/or a thermal cation generator.

* * * * *